United States Patent
Lopez

(10) Patent No.: US 10,176,507 B2
(45) Date of Patent: Jan. 8, 2019

(54) APPARATUS AND METHOD FOR A SELF-SERVICE DRUG LOCATOR KIOSK

(71) Applicant: Walmart Apollo, LLC, Bentonville, AR (US)

(72) Inventor: J. Guadalupe Lopez, Rogers, AR (US)

(73) Assignee: Walmart Apollo, LLC, Bentonville, AR (US)

(*) Notice: Subject to any disclaimer, the term of this patent is extended or adjusted under 35 U.S.C. 154(b) by 541 days.

(21) Appl. No.: 14/811,544

(22) Filed: Jul. 28, 2015

(65) Prior Publication Data

US 2016/0027089 A1    Jan. 28, 2016

Related U.S. Application Data

(60) Provisional application No. 62/029,996, filed on Jul. 28, 2014.

(51) Int. Cl.
  *G06Q 30/06*    (2012.01)
  *G06Q 50/22*    (2018.01)

(52) U.S. Cl.
  CPC ..... *G06Q 30/0631* (2013.01); *G06Q 30/0639* (2013.01); *G06Q 50/22* (2013.01)

(58) Field of Classification Search
  CPC . G06Q 30/0631; G06Q 30/0639; G06Q 50/22
  See application file for complete search history.

(56) References Cited

U.S. PATENT DOCUMENTS

| | | |
|---|---|---|
| 7,860,730 B1 | 12/2010 | Goodall |
| 7,941,325 B2 | 5/2011 | Heald |
| 8,688,473 B2 | 4/2014 | Roberts |
| 2003/0120384 A1* | 6/2003 | Haitin ............. A61G 12/001 700/242 |
| 2005/0091338 A1* | 4/2005 | de la Huerga ...... A61J 1/1437 709/217 |
| 2007/0088590 A1 | 4/2007 | Berkelhamer |
| 2011/0288883 A1 | 11/2011 | Knoth |
| 2012/0096023 A1* | 4/2012 | Park ............... G06F 17/3087 707/769 |
| 2012/0253830 A1 | 10/2012 | John |
| 2013/0054258 A1* | 2/2013 | Cohan ............... G06Q 30/02 705/2 |

* cited by examiner

*Primary Examiner* — Linh Giang Le
(74) *Attorney, Agent, or Firm* — Fitch, Even, Tabin & Flannery LLP

(57) ABSTRACT

Systems, apparatuses and methods are provided herein for a self-service drug locator interface. In one embodiment, a method of providing a self-service drug locator includes, receiving, from a customer, one or more identifiers associated with one or more drugs through a customer self-service drug locator interface. The system then selects a plurality of pharmacies meeting one or more search parameters, wherein the one or more search parameters comprise a maximum distance from a location or a geographical region. Inventories of the plurality of pharmacies are queried to determine whether the one or more drugs are in stock in each of the plurality of pharmacies. A list of recommended pharmacies is generated based on the querying of the inventories of the plurality of pharmacies and provided to the customer.

23 Claims, 4 Drawing Sheets

APPARATUS AND METHOD FOR A SELF-SERVICE DRUG LOCATOR KIOSK

RELATED APPLICATION(S)

This application claims benefit from U.S. Provisional Application No. 62/029,996, filed Jul. 28, 2014, which is incorporated by reference in its entirety herein.

TECHNICAL FIELD

This invention relates generally to pharmacies and medical prescriptions.

BACKGROUND

Traditionally, when a patient receives a medical prescription from a doctor, the patient would bring the prescription to a pharmacy to receive the medication. Systems have been implemented to allow hospitals to directly send a prescription order to a pharmacy of a patient's choosing. However, sometimes, when the patient arrives at the pharmacy, the patient is notified that one or more of the medicines in the prescription is not in stock at the pharmacy. Since patients' need for medicine is often urgent and time sensitive, they cannot always wait for several days for a medicine to be restocked at a pharmacy. In order to obtain his/her prescribed medication, a patient will have drive to one or more other pharmacies and wait in line to see if other pharmacies have their medication in stock. This process is often time consuming and frustrating to the patient, and can result in the patient purchasing medicine at a price higher than the price offered at the original pharmacy. This also causes a loss of revenue to the first pharmacy the patient visits.

BRIEF DESCRIPTION OF THE DRAWINGS

Disclosed herein are embodiments of apparatuses and methods for a user interface for self-service drug locator kiosk. This description includes drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses and methods are provided herein for a self-service drug locator kiosk. A method of providing a self-service drug locator user interface includes, receiving, from a customer, one or more identifiers associated with one or more drugs through a customer self-service drug locator interface. The system then selects a plurality of pharmacies meeting one or more search parameters, wherein the one or more search parameters comprise a maximum distance from a location or a geographical region. Inventories of the plurality of pharmacies are queried to determine whether the one or more drugs are in stock in each of the plurality of pharmacies. A list of recommended pharmacies is generated based on the querying of the inventories of the plurality of pharmacies and provided to the customer.

The drug locator user interface at a self-service kiosk allows a customer to locate one or more nearby pharmacies with their prescription medicine in stock before going to that pharmacy in person. The kiosk may be easily accessed by a customer without having to wait in-line to speak to a pharmacy staff. Providing a list of recommended pharmacies also allows the customer to choose a pharmacy location based on personal preferences that do not need to be entered into the system. The drug locator kiosk also encourages the customer to go to a pharmacy belonging to the same company such that the company does not lose revenue due to inventory shortage at one pharmacy location.

Figure 1:
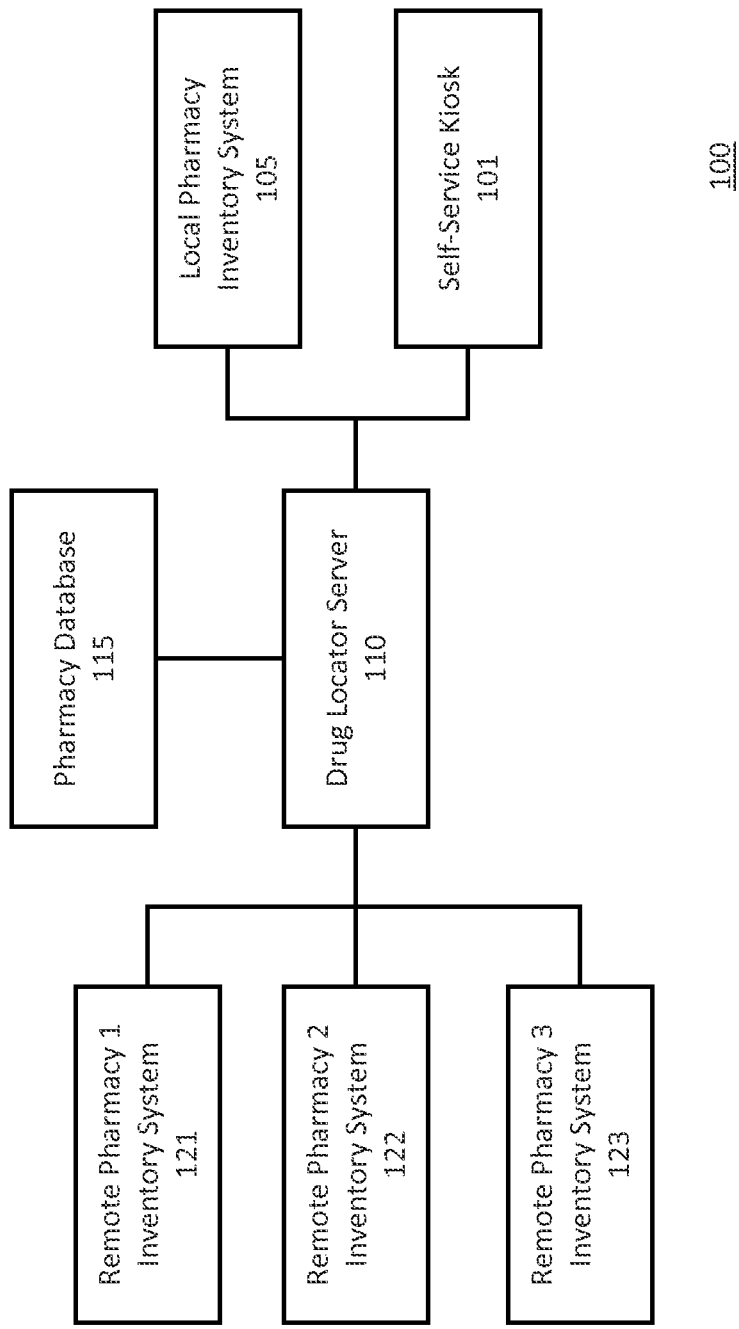
FIG. 1 is a block diagram of a system in accordance with several embodiments.

Referring now to FIG. 1, a system for providing a drug locator user interface is shown. The system 100 includes a self-service kiosk 101, a local pharmacy inventory system 105, a drug locator server 110, a pharmacy database 115, a remote pharmacy 1 inventory system 121, a remote pharmacy 2 inventory system 122, and a remote pharmacy 3 inventory system 123. While three remote pharmacy inventory systems are shown in FIG. 1, it is understood that the system 100 may include any number of remote pharmacy inventory systems accessible by the drug locator server 110.

The self-service kiosk 101 may be any processor-based device with one or more input and output devices. In some embodiments, the self-service kiosk 101 may be generally referred to as a user terminal. For example, the self-service kiosk 101 may be a computer inside a retail store such as a grocery store or a pharmacy for use by customers. The self-service kiosk 101 maybe located near the pharmacy counter, near the entrance of the store for easy access by customers, or at any other convenient location within or near the store. The self-service kiosk 101 may include a display device for displaying a drug locator user interface to the customer. The drug locator user interface may be a program installed on the self-service kiosk 101, a website access through a browser on the self-service kiosk 101, and/or a cloud-based application. The self-service kiosk 101 may include an input device which may be one or more of a touch screen, a keyboard, a mouse, a touch pad, a scanner, etc. for the user to enter drug or prescription information and/or search parameters. The self-service kiosk 101 may also include a network interface for communicating with at least one of the local pharmacy inventory system 105 and the drug locator server 110. In some embodiments, the self-service kiosk 101 may include a presence sensor such as an optical or weight sensor that determines whether a customer has left the kiosk. The interface may be configured to remove all information related to a user once the user leaves the kiosk. In some embodiments, the self-service kiosk 101 purges the information after a predetermined period of user inactivity.

In some embodiments, the self-service kiosk further includes a printer such as a laser printer or a thermal receipt printer for printing pharmacy information. Further details of the drug locator user interface and the self-service kiosk 101 is described in further detail below with reference to FIGS. 2 and 4.

The local pharmacy inventory system 105 is a database of drug availability information at a pharmacy. For example, the inventory system may include a list of all available drugs at the pharmacy and their available quantities. In some embodiments, the inventory system also includes information on brand-name drugs and their generic brand counterparts. In some embodiments, the local pharmacy inventory system 105 contains inventory information of the pharmacy that is in the same retail location as the self-service kiosk 101. In some embodiments, the local pharmacy refers to the pharmacy with the user's prescription. In some embodiments, the self-service kiosk 101 can access the information on the local pharmacy inventory system 105 through a local network or a direct data connection. In some embodiments, the self-service kiosk 101 accesses the information on the local pharmacy inventory system 105 through the drug locator server 110.

The drug locator server 110 facilities the exchange of information between the pharmacy inventory systems 105, 121, 122, and 123, and one or more self-service kiosks such as self-service kiosk 101. In some embodiments, the drug locator server 110 hosts a website and/or a cloud-based application that provides the drug locator user interface on the self-service kiosk 101. In some embodiments, the drug locator server 110 provides information requested by a drug locator program running on the self-service kiosk 101.

The pharmacy database 115 stores information on pharmacies served by the system 100. In some embodiments, the pharmacies in the pharmacy database 115 may include pharmacies in the same company and/or pharmacies with cooperative agreements. The pharmacy database 115 may store one or more of address, hours of operations, and average wait time of multiple pharmacies.

The remote pharmacy inventory systems 121, 122, and 123 may be similar to the local pharmacy inventory system 105, storing inventory information for their respective pharmacies. Each of the pharmacy inventory systems 105, 121, 122, and 123 may be a local storage at the pharmacy or a cloud-based database. While not shown in the FIG. 1, each remote pharmacy may also include one or more self-service kiosks similar to self-service kiosk 101. In which case, a pharmacy that is considered a remote pharmacy by the self-service kiosk 101 may be a local pharmacy to a kiosk located in the same retail location.

While the pharmacy inventory systems 105, 121, 122 and 123, the drug locator server 110, and the pharmacy database 115 are shown as separate elements, in some embodiments, these components of the system may be implemented through one or more of the same physical devices. For example, the drug locator server 110 and one or more of the pharmacy inventory systems 105, 121, 122 and 123 may be implemented on the same device(s). In some embodiments, the self-service kiosk 101 may be implemented with one or more of the local pharmacy inventory system 106, the drug locator server 110, and the pharmacy database 115. For example, the self-service kiosk 101 may be provided by the same system as the local pharmacy inventory system 105. In another example, the pharmacy database 115 or a copy of the pharmacy database 115 data may be stored on the self-service kiosk for faster look-up. In yet another example, the self-service kiosk may directly communicate with the remote pharmacy inventory systems 121, 122, and 123 and/or the pharmacy database 115 without a separate drug locator server 110.

Figure 2:
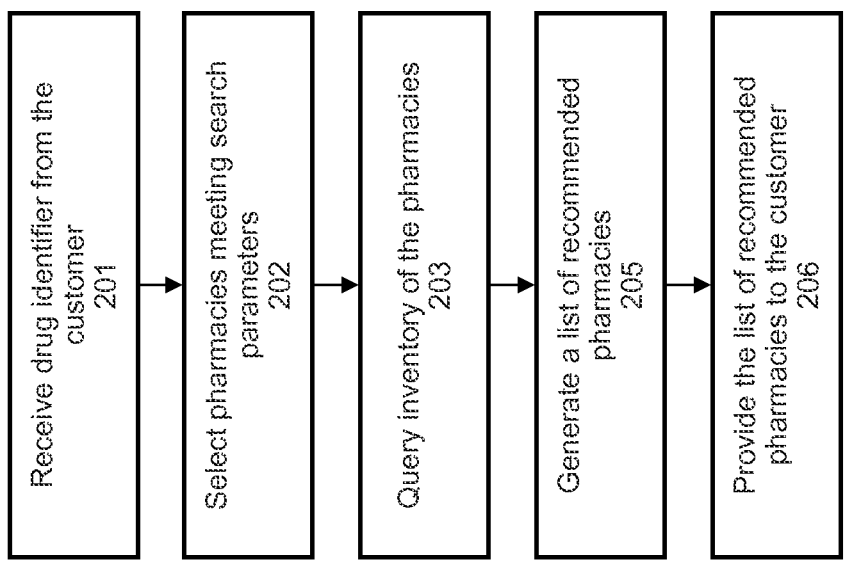
FIG. 2 is a flow diagram of a method in accordance with several embodiments.

Referring now to FIG. 2, a method of providing a self-service drug locator interface is shown. In step 201, the system receives a drug identifier from a customer via a self-service drug locator user interface. The drug identifier may be entered into a drug locator user interface by entering one or more of a drug identifier (e.g. National Drug Code (NDC), Generic Drug Indicator (GDI), etc), a drug name (e.g. Zocor), a customer identifier number (e.g. driver's license number), a customer name, a prescription identifier, a refill order identifier, etc. In some embodiments, the user also enters a quantity for the drug(s) entered in the self-service drug locator user interface. In some embodiments, the user can enter more than one drug identifier at a time. For example, multiple drug names, prescription identifiers, customer identifier etc. and/or a combination of the above may be entered for the same session. When a customer identifier number, a customer name, and/or customer log-in credential is entered, the system may retrieve one or more prescriptions associated with the customer to determine which drugs the customer is looking for and the needed quantity for each drug. The prescription may have been sent by a health care provider and/or may be a refill order of an earlier prescription order. When a prescription identifier or a refill order identifier is entered, the system may retrieve the one or more drugs associated with the prescription and their prescribed quantity. In some embodiments, identity verification may be required to access prescription information to protect patient privacy. For example, the user may need to log-in to a user account or scan an ID card. In some embodiments, the customer can enter one or more drug identifier in step 201 without identity verification.

In step 202, the system selects pharmacies meeting search parameters. The search parameters may include a maximum distance from location or a geographical region. For example, the system may automatically determine the location of the user based on the known kiosk or store location from which the use is accessing the interface. In some embodiments, the system may ask the user to either use a default location or enter a location. For example, the user may enter the location of their residence or work, etc. The search parameter also includes a maximum distance. In some embodiments, the system uses a default distance, such as 10 miles. In some embodiments, the user can enter a maximum distance he/she is willing to drive, for example, 20 miles. In some embodiments, the user may enter additional search parameters such as store type (e.g. Wal-Mart Supercenter, Wal-Mart Neighborhood Market, Wal-Mart Express Store, Sam's Warehouse Store, partner stores, etc.), hours of operations (e.g. open at 10 PM), etc. At step 202, the system searches through a list of pharmacies in a pharmacy database to select a number of pharmacies that meets the search parameters.

In step 203, the system queries the inventory of the pharmacies selected in step 202. The inventories of the selected pharmacies are queried to determine the availability of the drug(s) entered in step 201. In some embodiments, if two or more drugs are entered, the inventories are queried for the availability of all of the drugs entered in step 201. In some embodiments, step 203 is performed by querying the inventory systems of each pharmacy either directly or through a drug locator server.

In step 205, a list of recommended pharmacies is generated. The list of recommended pharmacies corresponds to the search results of steps 202 and 203. If one on drug is entered in step 201, the list of pharmacies may include pharmacies that have that drug in stock at the needed quantity. If two or more drugs are entered in step 201, the list of pharmacies may correspond to pharmacies with each of the drugs in stock at the needed quantity. That is, the system would determine which pharmacies the customer can go to fill their prescription(s) at one location.

In step 206, the list of recommended pharmacies is provided to the customer. The list generated at step 205 may be provided to the customer through displaying the list on a self-service kiosk. In some embodiments, the system can email or text the list to a customer upon request. In some embodiments, the system can print the list through a printer attached to a self-service kiosk to provide the listing as a paper printout. In some embodiments, the list is provided to a mobile device through an application installed on the mobile device. In some embodiments, the listing includes one or more of, pharmacy location, pharmacy hours of operation, available quantity of one or more drugs, and distance to the pharmacy for each pharmacy on the list. In some embodiments, the list is sorted by distance from a location in the search parameters.

In some embodiments, after the list of recommended pharmacies is displayed to the customer at the kiosk in step 206, the customer can selected one or more pharmacies on the list through the kiosk. The system will then only print, email or text the information of the one or more pharmacies selected by the user to the customer.

In some embodiments, after step 206, the user can select one of the recommended pharmacies to fill the prescription. The system may automatically transfer the user's prescription over to the designated pharmacy to be filled. The fulfilling pharmacy may begin to fill the prescription prior to the customer's arrival to the fulfilling pharmacy. In some embodiments, the system will provide a notification to the user when the prescription is ready for pickup at the fulfilling pharmacy. Notification may be sent via a phone call, a text message, an email, and the like. In some embodiments, the kiosk may provide an estimated time when the prescription will be ready for pickup at the designated pharmacy.

In the event that no pharmacy meeting the search parameters in step 202 has all of the one of more drugs entered in step 201 in stock, in some embodiments, the system may ask the user to modify their search parameters. For example, the user may increase the maximum search distance in the search parameters. In some embodiments, the system may provide a list of combination of two or more pharmacies though which the user can obtain all of the drugs entered in step 201. The recommended combination of pharmacies can be determined based on one or more of, available drug quantities, the pharmacies' proximity to a location in the search parameters, and the pharmacies' proximity to each other, etc.

In some embodiments, anytime during the process shown in FIG. 2, the self-service kiosk may determine whether the user is actively using the kiosk. For example, the user interface may lock after a period of inactivity and require the user to provide an indication of presence before the user is able to continue. In some embodiment, the indication of presence require user identity authentication such as entering a user name and/or password. In some embodiments, the kiosk includes a presence sensor for detecting whether the user is still standing in front of the kiosk. The kiosk may remove information associated with a user from being displayed once the user is determined to be inactive or have left the kiosk for a predetermined period of time, for example, 10 seconds. In some embodiments, when a user leaves the kiosk, drug and prescription information the user enters into the system is removed from the kiosk to protect the customer's privacy.

In some embodiments, after step 201, the kiosk may first query the inventory of the local pharmacy. If the local pharmacy can fulfill the prescription order (i.e. has all the prescribed drugs in stock), the kiosk will provide an indication to the user. In some embodiments, the user can request the prescription to be filled through the kiosk. In some embodiments, the kiosk may provide an estimated wait time before the prescription order is ready for pickup at the pharmacy counter. In some embodiments, step 202 and 206 is only performed when the local pharmacy does not have one or more of the requested drugs in stock.

Figure 3:
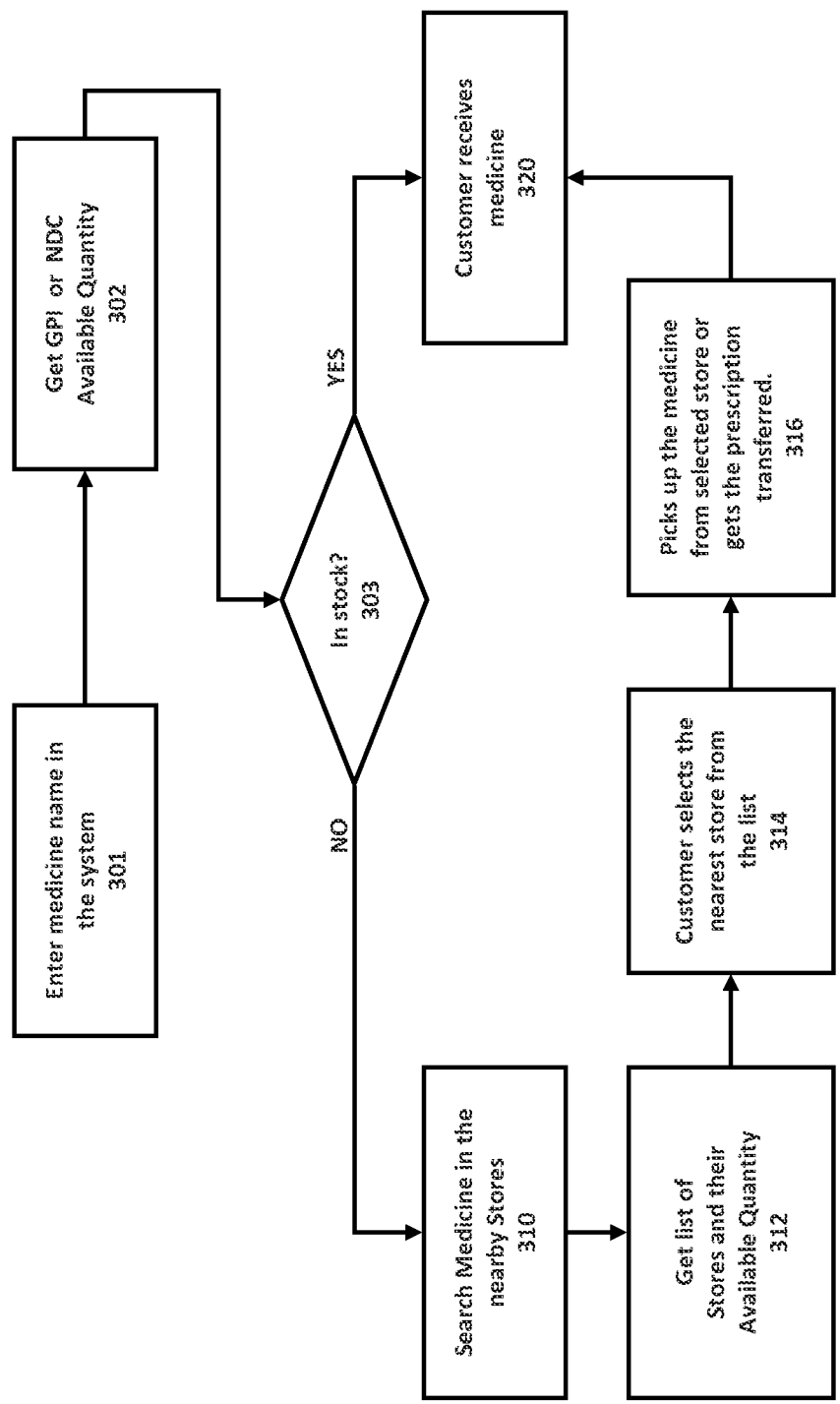
FIG. 3 is a flow diagram of a general process in accordance with several embodiments.

Now referring to FIG. 3, a process for fulfilling a prescription is shown. In step 301, the customer enters medicine name in the system. In step 302, the system determines a GPI or a DNC associated with the medicine name and determines the available quantity at a local pharmacy. In step 303, the system determines whether the medicine entered in step 301 is in stock locally. If the medicine is stock locally, the customer receives the medicine from the local pharmacy in step 320.

Otherwise, if the medicine is not available locally in step 303, in step 310, the system searches for medicine in nearby stores. In step 312, the system gets a list of stores and the available quantity of the medicine at each store. In step 314, the customer selects the nearest store from the list. In step 316, the customer is able to pick up the medicine from the selected store and/or get the prescription transferred to that store. In step 320, the customer receives the medicine at the store selected at step 314.

Figure 4:
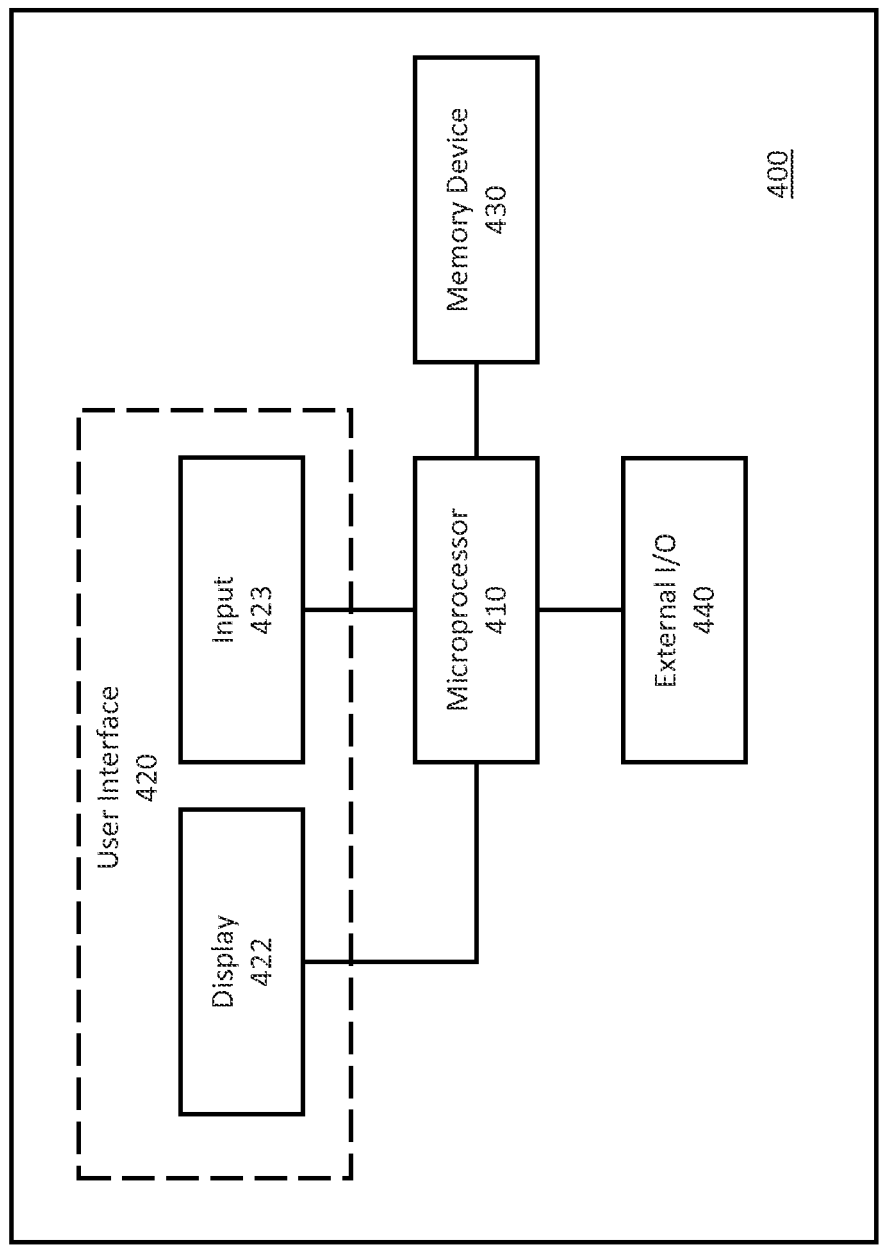
FIG. 4 is a block diagram of an apparatus in accordance with several embodiments.

Now referring to FIG. 4, an apparatus for providing a drug locator user interface is shown. The apparatus 400 may be a drug locator kiosk and may be generally referred to as a user terminal. The apparatus 400 includes a microprocessor 410, a user interface 420, a memory 430, and an external input/output (I/O) 440. The memory device 420 may store a set of instructions executable by the microprocessor 410. In some embodiments, the memory device stores a drug locator user interface program which, when executed by the microprocessor, displays the drug locator user interface on the display 422. In some embodiments, the memory device 430 includes instructions that causes the microprocessor 410 to access a drug locator user interface program stored on a remote sever accessed through the external I/O 440.

The user interface 420 includes a display 422 and an input 423. The display 422 may be any type of display device configured to show images of a user interface to a user. The display 422 may prompt a user to enter information needed to perform an inventory search. The display 422 may also show the result of the search to the user. The input 423 may be any input device such as a touch screen integrated with the display 422, a keyboard, a mouse, and/or a touch pad, etc. The input 423 is configured to allow the user to interact with the drug locator user interface and enter one or more drug identifiers and/or search parameters to perform a search.

The external I/O 440 may be any data connection such as a direct data cable, a local network adapter, an internet adapter, and wi-fi adapter, and the like. The external I/O 440 is configured to be used by the microprocessor to retrieve information needed to provide the drug locator user interface to a user. For example, based on the inputs received in through the user interface 420, the microprocessor 410 may query the inventories of other pharmacies through the external I/O 440.

In some embodiments, the apparatus 400 may also include a printer (not shown) for printing information on recommended pharmacies upon user's request. In some embodiments, the apparatus 400 may further include a presence sensor for determining whether a user has left the kiosk such that the user's information can be removed to protect his/her privacy.

In some embodiments, the apparatus 400 is a dedicated machine for providing the drug locator user interface. In some embodiments, the apparatus 400 may also provide other functions for in-store shoppers. For example, the kiosk may also provide In one embodiment, a computer implemented method for providing a self-service drug locator is provided. The method includes the steps of: receiving, from a customer, one or more identifiers associated with one or more drugs through a customer self-service drug locator interface, selecting a plurality of pharmacies meeting one or more search parameters, wherein the one or more search parameters comprises a maximum distance from a location or a geographical region, querying inventories of the plurality of pharmacies to determine whether the one or more drugs are in stock in each of the plurality of pharmacies, generating a list of recommended pharmacies based on the querying of the inventories of the plurality of pharmacies, and providing the list of recommended pharmacies to the customer.

In one embodiment, an apparatus for providing a customer self-service drug locator is provided. The apparatus includes a processor-based device, and a non-transitory computer readable medium storing a set of instructions executable by the processor-based device. The set of instructions executable by the processor-based device and configured to cause the processor-based device to perform the steps of: receiving, from a customer, one or more identifiers associated with one or more drugs through a customer self-service drug locator interface, selecting a plurality of pharmacies meeting one or more search parameters, wherein the one or more search parameters comprises a maximum distance from a location or a geographical region, querying inventories of the plurality of pharmacies to determine whether the one or more drugs are in stock in each of the plurality of pharmacies, generating a list of recommended pharmacies based on the querying of the inventories of the plurality of pharmacies, and providing the list of recommended pharmacies to the customer.

In one embodiment, an apparatus for providing a self-service drug locator kiosk is provided. The self-service drug locator kiosk includes a display device providing a self-service drug locator interface, a user input device configured to receive, from a customer, one or more search parameters and one or more identifiers associated with one or more drugs, a network interface for querying inventories of a plurality of pharmacies meeting the one or more search parameters to determine whether the one or more drugs are in stock in each of the plurality of pharmacies, wherein the one or more search parameters comprises a maximum distance from a location or a geographical region. The display device displays a list of recommended pharmacies to the customer based on a result of the querying of the inventories of the plurality of pharmacies.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A computer implemented method for providing a self-service drug locator comprising:
   receiving, from a customer, one or more identifiers associated with one or more drugs through a customer self-service drug locator interface displayed on a self-service kiosk comprising a display screen and a weight sensor;
   selecting a plurality of pharmacies meeting one or more search parameters, wherein the one or more search parameters comprises a maximum distance from a location or a geographical region;
   querying inventories of the plurality of pharmacies to determine whether the one or more drugs are in stock in each of the plurality of pharmacies;
   generating a list of recommended pharmacies based on the querying of the inventories of the plurality of pharmacies;
   providing the list of recommended pharmacies to the customer on the display screen; and
   detecting, with the weight sensor of the self-service kiosk, whether the customer is present at the self-service kiosk providing the self-service drug locator interface; and
   removing information associated with the customer from the display screen when the weight sensor detects that the customer has left the self-service kiosk.

2. The computer implemented method of claim 1, wherein the one or more identifiers comprises one or more of: a drug identifier, a drug name, a customer identifier number, a customer name, a prescription identifier, and a refill order identifier.

3. The computer implemented method of claim 1, further comprising:
   retrieving one or more prescriptions comprising one or more drug identifiers and associated dosage information using the one or more identifiers.

4. The computer implemented method of claim 1, wherein, in the event that the one or more identifiers are associated with two or more drugs, the list of recommended pharmacies corresponds to pharmacies having all of the two or more drugs in stock.

5. The computer implemented method of claim 1, wherein, the list of recommended pharmacies comprises availability information for each of the one or more drugs at each of the recommended pharmacies.

6. The computer implemented method of claim 1, wherein the list of recommended pharmacies is sorted by a distance from the location or the geographical region.

7. The computer implemented method of claim 1, wherein the one or more search parameters comprises one or more of a default location and a default distance.

8. The computer implemented method of claim 1, further comprising: receiving, through the customer self-service drug locator interface, at least one of the one or more search parameters.

9. The computer implemented method of claim 1, wherein providing the list of recommended pharmacies to the customer comprises providing information of the recommended pharmacies via short message service (SMS) text message, email, voicemail, application, and paper printout.

10. The computer implemented method of claim 1, further comprising:
    receiving a selection of a selected pharmacy from the list of recommended pharmacies from the customer, and transferring one or more prescriptions associated with the one or more identifiers to the selected pharmacy to fill.

11. The computer implemented method of claim 10, further comprising:
sending a notification to the customer when the prescription is ready for pickup at the selected pharmacy.

12. An apparatus for providing a customer self-service drug locator comprising:
a processor-based device; and
a non-transitory computer readable medium storing a set of instructions executable by the processor-based device and configured to cause the processor-based device to perform the steps of:
receiving, from a customer, one or more identifiers associated with one or more drugs through a customer self-service drug locator interface displayed on a self-service kiosk comprising a display screen and a weight sensor;
selecting a plurality of pharmacies meeting one or more search parameters, wherein the one or more search parameters comprises a maximum distance from a location or a geographical region;
querying inventories of the plurality of pharmacies to determine whether the one or more drugs are in stock in each of the plurality of pharmacies;
generating a list of recommended pharmacies based on the querying of the inventories of the plurality of pharmacies;
providing the list of recommended pharmacies to the customer on the display screen; and
detecting, with the weight sensor of the self-service kiosk, whether the customer is present at the self-service kiosk providing the self-service drug locator interface; and
removing information associated with the customer from the display screen when the weight sensor detects that the customer has left the self-service kiosk.

13. The apparatus of claim 12, wherein the one or more identifiers comprises one or more of: a drug identifier, a drug name, a customer identifier number, a customer name, a prescription identifier, and a refill order identifier.

14. The apparatus of claim 12, wherein the processor-based device further performs the step of:
retrieving one or more prescriptions comprising one or more drug identifiers and associated dosage information using the one or more identifiers.

15. The apparatus of claim 12, wherein, in the event that the one or more identifiers are associated with two or more drugs, the list of recommended pharmacies corresponds to pharmacies having all of the two or more drugs in stock.

16. The apparatus of claim 12, wherein, the list of recommended pharmacies comprises availability information for each of the one or more drugs at each of the recommended pharmacies.

17. The apparatus of claim 12, wherein the list of recommended pharmacies is sorted by a distance from the location or the geographical region.

18. The apparatus of claim 12, wherein the one or more search parameters comprises one or more of a default location and a default distance.

19. The apparatus of claim 12, wherein the processor-based device further performs the step of: receiving, through the customer self-service drug locator interface, at least one of the one or more search parameters.

20. The apparatus of claim 12, wherein providing the list of recommended pharmacies to the customer comprises providing information of the recommended pharmacies via short message service (SMS) text message, email, voicemail, application, and paper printout.

21. The apparatus of claim 12, wherein the processor-based device further performs the steps of:
receiving a selection of a selected pharmacy from the list of recommended pharmacies from the customer; and
transferring one or more prescriptions associated with the one or more identifiers to the selected pharmacy to fill.

22. The apparatus of claim 21, wherein the processor-based device further performs the step of:
sending a notification to the customer when the prescription is ready for pickup at the selected pharmacy.

23. A self-service drug locator kiosk comprising:
a display device providing a self-service drug locator interface;
a weight sensor configured to determine whether a customer is present at the self-service kiosk providing the self-service drug locator interface;
a user input device configured to receive, from the customer, one or more search parameters and one or more identifiers associated with one or more drugs; and
a network interface for querying inventories of a plurality of pharmacies meeting the one or more search parameters to determine whether the one or more drugs are in stock in each of the plurality of pharmacies, wherein the one or more search parameters comprises a maximum distance from a location or a geographical region;
wherein the display device displays a list of recommended pharmacies to the customer based on a result of the querying of the inventories of the plurality of pharmacies; and
wherein the display device is configured to remove the display of information associated with the customer when the customer leaves the self-service kiosk according to the weight sensor.

* * * * *